United States Patent [19]

Schaefer

[11] Patent Number: 5,018,712
[45] Date of Patent: May 28, 1991

[54] PATIENT SUPPORTING MEANS HAVING A PIVOTABLE PATIENT SUPPORTING PLATE

[75] Inventor: Willi Schaefer, Erlangen, Fed. Rep. of Germany

[73] Assignee: Siemens Aktiengesellschaft, Munich, Fed. Rep. of Germany

[21] Appl. No.: 539,899

[22] Filed: Jun. 18, 1990

[30] Foreign Application Priority Data

Jun. 30, 1989 [EP] European Pat. Off. ........ 89111990.1

[51] Int. Cl.$^5$ .......................................... A61G 13/00
[52] U.S. Cl. .................................................. 269/323
[58] Field of Search ................ 269/322, 323; 378/209; 108/4–8

[56] References Cited

U.S. PATENT DOCUMENTS

| 3,149,229 | 9/1964 | Morel . | |
|---|---|---|---|
| 3,609,357 | 9/1971 | Jones . | |
| 4,475,072 | 10/1984 | Schwehr et al. . | |
| 4,568,071 | 2/1986 | Rice . | |
| 4,579,323 | 4/1986 | Brendl et al. ...................... | 269/323 |
| 4,674,505 | 6/1987 | Pauli et al. . | |

FOREIGN PATENT DOCUMENTS

| 0294679 | 12/1988 | European Pat. Off. . |
|---|---|---|
| 2612728 | 10/1976 | Fed. Rep. of Germany . |
| 2636746 | 3/1978 | Fed. Rep. of Germany . |
| 2759079 | 7/1979 | Fed. Rep. of Germany . |
| 3222332 | 12/1983 | Fed. Rep. of Germany . |
| 1191471 | 10/1959 | France . |
| 1949182 | 11/1970 | German Democratic Rep. . |

OTHER PUBLICATIONS

Siemens Aktiengesellschaft Bereich Medizinische Technik-Erlangen Brochure "Siregraph D1 Universal-Rontgen-Diagnostik-gerat Mikroprozessorgesteuert", fern–und nahbedienbar pp. 1–15.

Primary Examiner—Robert C. Watson
Attorney, Agent, or Firm—Hill, Van Santen, Steadman & Simpson

[57] ABSTRACT

Patient supporting means having a patient supporting surface member that is mounted on a base by means of at least two longitudinal guides so as to be pivotable around a horizontal swiveling axis S. Central axes of the longitudinal guides are positioned within a plane E that extends perpendicularly to the swiveling axis X. The axes of the longitudinal guides describe an angle α that is less than 180°. The longitudinal guides are pivotable about axes that extend parallel to the swiveling axis 5.

15 Claims, 2 Drawing Sheets

PATIENT SUPPORTING MEANS HAVING A PIVOTABLE PATIENT SUPPORTING PLATE

BACKGROUND OF THE INVENTION

The present invention is generally directed to patient supporting means such as patient tables. More particularly, the invention relates to a patient supporting table having a patient supporting plate that is attached to a supporting element, such as a base, and that is pivotable about a horizontal axis.

Such patient supporting means are required, for example, in x-ray diagnostics, radiation therapy, urology, and surgery in order to provide for adjustable positioning of a patient in a suitable way for diagnostic or therapeutic purposes.

A patient supporting means of the type to which the invention relates is disclosed in conjunction with an x-ray diagnostic installation in a document entitled "SIEREGRAPH D1", Order No. A91001-M1018-G531-01, that is published by Siemens AG, a German company. In the disclosed means, a patient supporting plate is mounted on the straight edge side of a semicircular member whose curved edge side is slidingly received in a corresponding bearing means of a base member. The straight edge side describes the longitude of the patient supporting plate. The semicircular member is received in the bearing means such that the straight edge and, hence, the patient supporting plate mounted thereon are pivotable about a horizontal swiveling axis that extends through the radial center of the semicircular member and tranversely relative to the patient supporting plate. As a result, the patient supporting plate can be pivoted with high precision about the swiveling axis even given pivoting angles of more than 180°. Such large pivoting angles, however, are required only in certain instances.

It can be appreciated that the disclosed device requires a large overhead clearance to accommodate the patient supporting plate when it is pivoted through large rotations. Further, the disclosed table involves a rather considerable structural and manufacture-associated outlay to build and install, and this in turn translates into increased costs.

SUMMARY OF THE INVENTION

The invention provides a patient supporting means, such as a table, with a patient supporting plate that has adequately precise pivotability between pivoting angles on the order of magnitude of approximately ±20°.

To this end, the invention provides, in an embodiment, a patient supporting means comprising:
a) a surface member on which a patient can be supported;
b) a base on which the surface member is mounted;
c) a guide arrangement mounting the surface member on the base, the guide arrangement including at least two longitudinal guides forming a longitudinal guide pair, each longitudinal guide comprising a guide member and a guide support member, the guide members being displaceably received within the guide support members so that the guide members are capable of axial movement within the guide support members, the guide members of each longitudinal guide pair being positioned on opposite sides of the surface member so as to define a V-shape.

An advantage of using this type of guide arrangement is that commercially available components can be used and thus, only minor structural, manufacturing, and financial outlays are required. Moreover, the overhead clearance required to accommodate the supporting means is considerably less than that needed for the above-described prior art devices.

For situations wherein a therapeutically and/or diagnostically relevant region of a patient lying on the patient supporting surface should retain its position during pivoting of the patient supporting surface, in one embodiment of the invention, it is provided that the swiveling axis of the patient supporting surface falls within the V-shaped angle described by the axes of the longitudinal guide members. The patient is placed on the patient supporting surface so that the swiveling axis extends through the diagnostically or therapeutically relevent region.

Although a stable support of the patient supporting surface is guaranteed because the axes of the guide members are situated in a common plane, in an embodiment, the invention provides, for the sake of increased stability, that several planes containing other longitudinal guide pairs are arranged in spaced apart fashion along the longitude of the surface member.

Also, for the sake of increased stability, more than two longitudinal guides are provided on a side of the patient supporting surface in a further embodiment of the invention, whereby the central axes of the longitudinal guides are arranged in two planes that extend proceeding parallel to the swiveling axis and describe the V-shaped angle with one another.

In one embodiment, the invention provides that the guide support members are pivotable about axes that intersect, or nearly intersect, the central axes of the corresponding longitudinal guides. An advantage that is thereby achieved is that the patient supporting surface and the base are parallel to one another in every position during pivoting of the surface. The region between patient supporting surface and base remains largely constant. Moreover, additional torques about the central axes of the longitudinal guides are avoided. Further, the required pivotability of the central axes of the longitudinal guides can be structurally realized with little outlay.

It is also provided in a preferred embodiment of the invention that the guide members are secured to the patient supporting surface and the guide supporting members are pivotably secured to the base. In comparison to an opposite construction, the advantage derives that the overall geometrical dimensions, i.e. the volume surrounding the patient supporting means with the pivotable patient supporting surface is significantly smaller.

In a further embodiment, the invention provides that the guide members are formed by guide rails and the guide support members are formed by bearing devices that accept the guide rails. For example, the longitudinal guides distributed by Star Kugelhalter, Schweinfurt, Federal Republic of Germany under the designation "STAR" 1601-15 can be employed.

These and other features of the invention will become clear with reference to the following detailed description of the preferred embodiments and accompanying drawings.

DETAILED DESCRIPTION OF THE PRESENTLY PREFERRED EMBODIMENTS

Figure 1:
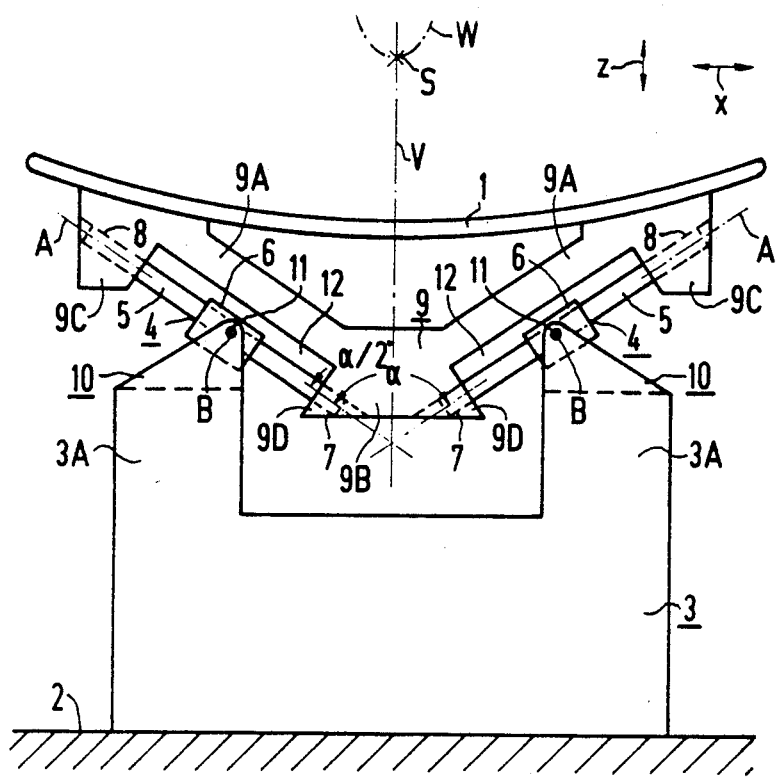
FIG. 1 is an end view of a patient supporting means embodying principles of the invention.
Figure 2:
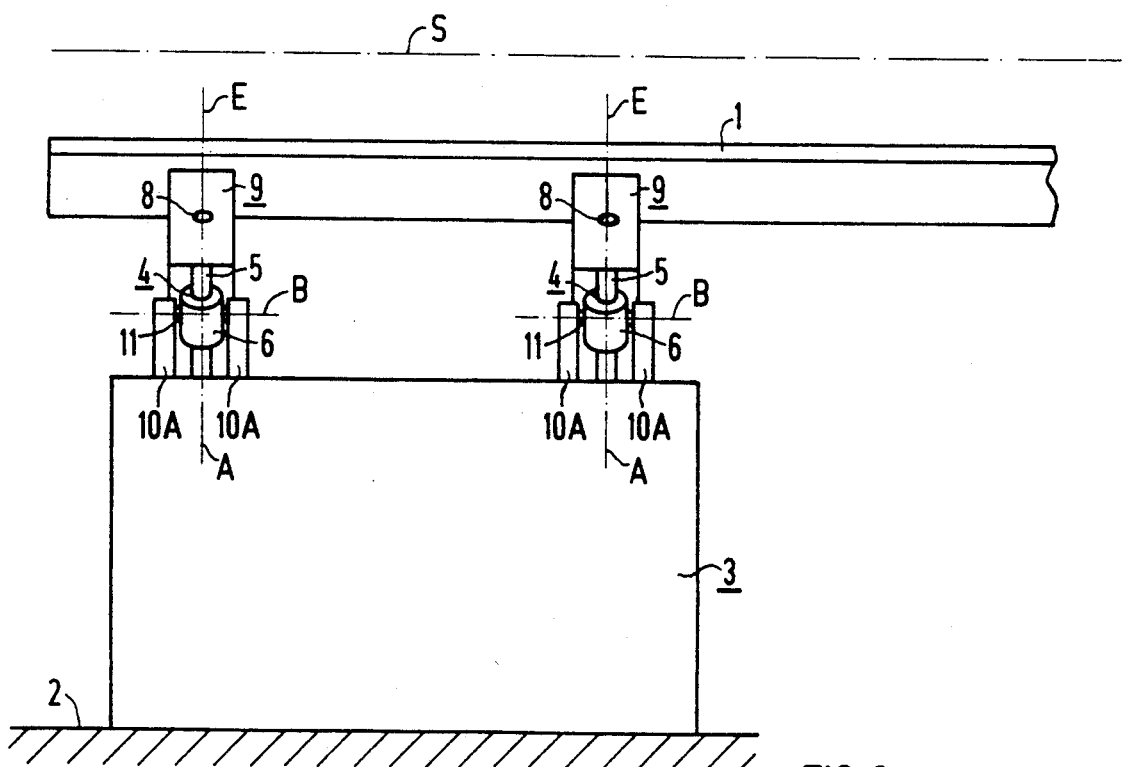
FIG. 2 is a side view of the patient supporting means of FIG. 1.

In FIGS. 1 and 2 there is illustrated a patient supporting table comprising a patient supporting plate 1 that is pivotable about a swiveling axis S and that serves as a surface member on which a patient can be supported. The axis S is positioned above the patient supporting plate 1 and runs parallel to a longitudinal axis of the patient supporting table. The plate 1 is supported on and secured to a pedestal or base 3 that rests on a floor 2.

As illustrated, the patient supporting plate 1 is secured to the pedestal 3 via braces or transverse supporting elements 9 and longitudinal guides 4. Essentially, the braces 9 are secured to the patient supporting plate 1 and the longitudinal guides secure the braces 9 to the pedestal 3.

As also illustrated, each longitudinal guide 4 comprises a straight guide member 5 that preferably is a cylindrically-shaped rod. The guide member 5 is slidingly received in a guide support member 6 that includes a bore adapted to the diameter of the cross-section of the guide element 5.

The guide support member 6 can comprise a plain sleeve shaped bearing or a sleeve-shaped longitudinal ball bearing such as that disclosed in German published application No. 19 49 182. The guide member 5 therefore interacts with guide support member 6 such that they are displaceable relative to each other along a central axis A of the longitudinal guide 4 and of the guide member 5.

As illustrated, each brace 9 is substantially V-shaped including two outwardly and upwardly extending legs 9A that are joined at an apex 9B. Upper ends of the legs 9A are secured to opposite lateral sides of the patient supporting plate 1. The Vshape of each brace 9 is positioned in a plane E that extends transversely, preferably at a right angle, to the longitudinal axis of the patient supporting table.

Each leg 9A includes a cut out 12 on an outside portion thereof so that a slightly outwardly and downwardly extending portion 9C that extends from the upper end adjacent the patient supporting plate 1 is formed. Similarly, an outwardly extending portion 9D is formed at the apex 9B of the V-shape.

As illustrated, a bore 8 is formed in the extension 9C of each leg 9A and a bore 7 is formed in the extension 9D of each leg 9A. These bores 7 and 8 are aligned along a common axis.

Received within each pair of bores 7 and 8 is one guide member 5. Thus, the common axis of the bores 7 and 8 is the same as the central axis A of the guide member 5 and the associated longitudinal guide 4.

Because each longitudinal guide 4 extends substantially parallel to a leg 9A of a brace 9, it is understood that each brace 9 includes a pair of longitudinal guides 4, the central axes A of which fall within the common plane E of the legs 9A of the brace 9.

As can also be seen, the axes A of each pair of longitudinal guides describe an angle $\alpha$ that is less than 180°. The swiveling axis S extends within this angle $\alpha$ and transverse to the respective plane E.

The guide support members 6, in turn are secured to two upstanding arms 3A of the pedestal 3. Each upstanding arm includes a fork member 10 that comprises two upwardly extending parallel plates 10A.

Each guide support member 6 is pivotally secured between a pair of plates 10A by means of pins 11 that extend out from the guide support member 6 and into suitable bores or openings in the plates 10A. As such, each guide support member is pivotable about an axis B described by its pins 11, which axis extends parallel to the swiveling axis S and preferably intersects the central axis A of its associated longitudinal guide 4.

It can be seen that the cut-out 12 of each leg 9A is made large enough to permit relative displacement of the associated guide support member 6 along the axis A of the associated guide member 5.

It can be appreciated that while the patient supporting table of FIGS. 1 and 2 is illustrated as using two braces 9, any number of suitably designed braces can be used. It is important, however, to maintain the planes E of the braces 9 parallel to each other, and to impart an identical angle $\alpha$ to each pair of longitudinal guides 4 associated with each brace 9.

As a result of the described construction of the patient supporting means, the patient supporting plate 1 is pivotable around the swiveling axis S that extends parallel to the longitudinal axis of the patient support plate 1. This, however, does not mean that the swiveling axis S is stationary during the pivoting process. On the contrary, what is meant herein by the term swiveling axis S is that axis that extends perpendicular to the planes E, intersects an angle bisector V of the angle $\alpha$ and experiences the least dislocation during the pivoting process.

When pivoting the patient supporting plate 1, the guide members 5 slidingly displace within the guide support members 6 that simultaneously effect a pivoting motion about their axes B. The swiveling axis S, that given a non-pivoted patient supporting plate, assumes the position shown in FIG. 1, displaces along a path W illustrated by broken lines in FIG. 1. The course of the path W is to be understood only qualitatively and not true-to scale.

In a prototype executed in conformity with FIGS. 1 and 2 wherein the angle $\alpha$ was 128° and the spacing of the axes B of the pairs of longitudinal guides 4 respectively was 310mm, the swiveling axis S lay 374mm above the intersections of the central axes A of the longitudinal guides 4. For pivoting angles of $\pm 15°$ in the prototype, a vertical dislocation of the swiveling axis S (illustrated by arrow Z) of not more than +11mm occured. A horizontal dislocation (illustrated by arrows X) of not more than $\pm 15$mm occured. The dislocation of the swiveling axis S is thus usually negligible in practice.

As a consequence of the fact that the planes E containing the central axes A of the longitudinal guides 4 in the prototype were at a distance of several hundred millimeters from one another, and as a consequence of employing two pairs of longitudinal guides 4, a mechanically stable support of the patient supporting plate 1 was achieved.

Figure 3:
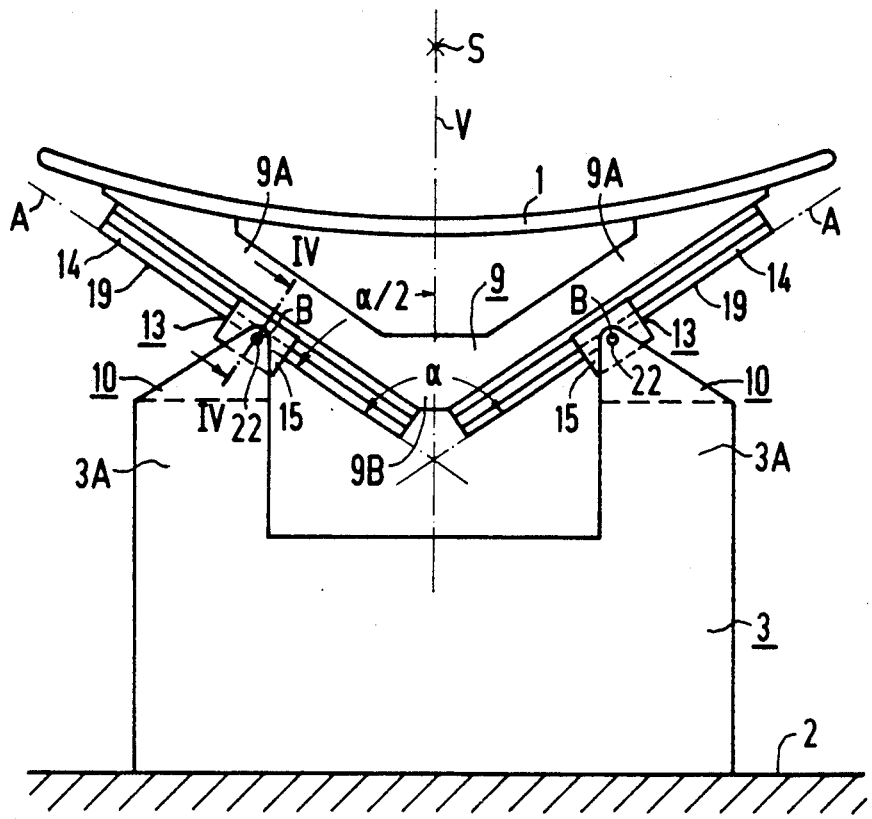
FIG. 3 is an end view of another patient supporting means embodying principles of the invention.
Figure 4:
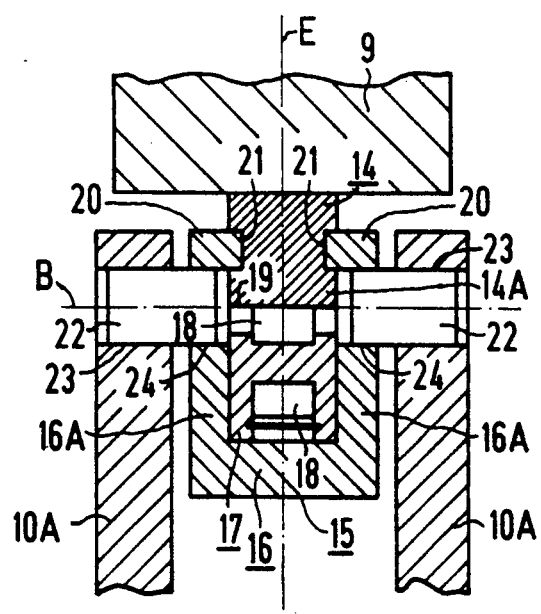
FIG. 4 is an enlarged sectional of the patient supporting means of FIG. 3 taken generally along the line IV—IV.

Another patient supportint table is illustrated in FIGS. 3 and 4. The exemplary embodiment of FIGS. 3 and 4 essentially differs from that set forth in FIGS. 1 and 2 in that the longitudinal guides 4 are replaced by different longitudinal guides 13. Therefore, in all other respects the tables are identical and identical reference numerals are used to identify identical components.

Each of the longitudinal guides 13 comprises a straight guide rail 14 having an approximately double-T-shaped cross-section as the counterpart to the guide member 5. The guide rails 14 are screwed to the braces 9 in a way that is not illustrated. Other suitable securing schemes, however, can be used. For example, the guide rails 14 can be unitarily formed with the braces 9.

Each of the longitudinal guides 13 comprises a bearing shoe 15 as the counterpart to the guide support member 6. The shoe 15 has a U-shaped base member 16 between whose legs a longitudinal rolling bearing 17 having cylindrical rolling members 18 is secured. Such a longitudinal rolling bearing also referred to as a circulating roller shoe, can, for example, be obtained from the SKF Company located in Schweinfurt, Federal Republic of Germany.

The rolling members 18 of the longitudinal rolling bearings 17 roll on the outside—formed as a planar running surface 19—of a flange 14A of the guide rail 14 facing away from the brace 9. The center line of the rolling surface 19 thereby represents a central axis A of a longitudinal guide 13.

The legs 16A of the U-shaped base member 16 have their free ends provided with inwardly directed projections 20 that engage into channels 21 limited by the inside surfaces of the flange of the guide rail 14 and by the lateral surfaces of the web of the guide rail 14. When pivoting the patient supporting plate 1 around the swiveling axis S, the rolling members 18 of the longitudinal rolling bearings 17 roll off on the running surfaces 19 to the guide rails 14. Simultaneously, the projections 20 glide in the channels 21. The bearing shoes 15 thus embrace the guide rails 14 with a form-fit such that forces can be transmitted in arbitrary directions.

The bearing shoes 15 are flexibly seated in the fork legs 10 by means of pins 22 that are received into corresponding bores 23 and 24 of the fork legs 10 or, respectively, of the base members 16 of the bearing shoes. The bearing shoes 15 are flexibly seated such that the running surfaces 19 of the guide rails contain the axes B that correspond to central axes of the pins 22.

The exemplary embodiments are directed only to patient supporting means wherein the patient supporting plate 1 is pivotable around a swiveling axis S that extends parallel to its longitudinal axis. The invention, however, can also be used in patient supporting means whose patient supporting plate is pivotable around some other swiveling axis, for example, a swiveling axis that extends transversely relative to the longitudinal axis of the supporting plate. Moreover, it can be provided that the guide members 5 or, respectively, 14 of the longitudinal guides 4 or, respectively, 13 are secured to the pedestal or base 3 and the guide support members 6, or, respectively, 15 are secured to the patient supporting plate 1 or to the braces 9.

While a preferred embodiment has been shown, modifications and changes may become apparent to those skilled in the art which shall fall within the spirit and scope of the invention. It is intended that such modifications and changes be covered by the attached claims.

I claim:

1. A patient supporting means comprising:
   (a) a surface member on which a patient can be supported, said surface member being pivotable about a swiveling axis;
   (b) a base on which the surface member is mounted;
   (c) a guide arrangement mounting the surface member on the base, the guide arrangement including at least two longitudinal guides the longitudinal guides each comprising a straight guide member and a guide support member that cooperates with the guide member such that the guide member and the guide support member are displaceable relative to one another along a central axis of the longitudinal guide associated therewith, the central/axis of each longitudinal guide pair being aligned in a plane that extends at a right angle relative to the swiveling axis of the surface member, the central axes of/the longitudinal guides forming an angle α of less than 180°.

2. The patient supporting means of claim 1, wherein the central axes of the longitudinal guides are pivotable around axes that extend parallel to the swiveling axis of the surface member.

3. The patient supporting means of claim 1, wherein the swiveling axis of the surface member lies above the surface member and within the angle α described by the central axes of the longitudinal guides.

4. The patient supporting means of claim 1, wherein the planes containing the central axes of the longitudinal guides are positioned in spaced apart fashion.

5. The patient supporting means of claim 1, comprising more than two longitudinal guides the central axes of the longitudinal guides being arranged in two longitudinal planes that extend parallel to the swiveling axis and describe the angle α.

6. The patient supporting means of claim 2, wherein the/axis about which each longitudinal guide is pivotable extends through the central axis of the corresponding longitudinal guide.

7. The patient supporting means of claim 1, wherein the guide members are attached to the surface member and the guide support members are attached to the base.

8. The patient supporting means of claim 1, wherein each guide support member is pivotable about the axis about which the longitudinal guide is pivotable.

9. The patient supporting means of claim 1, wherein the guide members comprise cylindrical rods.

10. The patient supporting means of claim 1, wherein the guide support members comprise sleeve bearings.

11. The patient supporting means of claim 1, wherein the guide members comprise rails.

12. A patient supporting table, comprising:
    (a) a patient supporting surface member;
    (b) a base on which said surface member is mounted; and
    (c) means for pivotably mounting said surface member to said base so that said surface member pivots around a swiveling axis, said means comprising one or more pairs of longitudinal guides, each longitudinal guide comprising a central axis, a guide member secured to said surface member, a guide support member pivotably secured on said base, said guide member being slidingly received in said guide support member, and each longitudinal guide pair describing a V-shape positioned perpendicular to said swiveling axis.

13. The patient supporting means of claim 1, wherein two longitudinal guides form a respective longitudinal guide pair, the central axes of the longitudinal guides of each longitudinal guide pair describing the angle α and being arranged in a common plane extending at right angles to the swiveling axis of the surface member.

14. The patient supporting means of claim 13, wherein at least two longitudinal guide pairs are provided, the central axes of the longitudinal guides of each of the longitudinal guide pairs describing an identical angle α.

15. The patient supporting means of claim 1 wherein the guide support members positively engage the guide members.

* * * * *